United States Patent
Andriacchi et al.

(10) Patent No.: US 6,770,099 B2
(45) Date of Patent: Aug. 3, 2004

(54) FEMORAL PROSTHESIS

(75) Inventors: Thomas Andriacchi, Stanford, CA (US); Ron Donkers, Warsaw, IN (US); James Harris, Warsaw, IN (US); Audrey Patmore, Winona Lake, IN (US); Scott Steffensmeier, Warsaw, IN (US); Shinro Takai, Kyoto (JP); Linggawati Tanamal, Fort Wayne, IN (US); Peter Walker, New York, NY (US)

(73) Assignee: Zimmer Technology, Inc., Chicago, IL (US)

( * ) Notice: Subject to any disclaimer, the term of this patent is extended or adjusted under 35 U.S.C. 154(b) by 0 days.

(21) Appl. No.: 10/299,436

(22) Filed: Nov. 19, 2002

(65) Prior Publication Data

US 2004/0098132 A1 May 20, 2004

(51) Int. Cl.[7] .................................................. A61F 2/38
(52) U.S. Cl. .................................. 623/20.35; 623/20.14

(58) Field of Search ........................... 623/20.14, 20.35, 623/20.16, 20.21, 20.15, 20.31, 20.26, 21.11

(56) References Cited

U.S. PATENT DOCUMENTS

| | | | | |
|---|---|---|---|---|
| 5,549,688 A | * | 8/1996 | Ries et al. ................ | 623/20.35 |
| 5,681,354 A | * | 10/1997 | Eckhoff .................... | 623/20.35 |
| 6,056,779 A | * | 5/2000 | Noyer et al. .............. | 623/20.32 |
| 6,123,729 A | * | 9/2000 | Insall et al. ............... | 623/20.31 |
| 6,152,960 A | * | 11/2000 | Pappas ..................... | 623/20.31 |
| 6,235,060 B1 | * | 5/2001 | Kubein-Meesenburg et al. | 623/20.31 |
| 6,402,786 B1 | * | 6/2002 | Insall et al. ............... | 623/20.35 |

* cited by examiner

*Primary Examiner*—Alvin Stewart
(74) *Attorney, Agent, or Firm*—Jonathan D. Feuchtwang; Zimmer Technology, Inc.

(57) ABSTRACT

A femoral component for a prosthetic knee implant system. The femoral component comprises medial and lateral condyles, wherein the height of the medial condyle is greater than the height of the lateral condyle.

11 Claims, 3 Drawing Sheets

FEMORAL PROSTHESIS

BACKGROUND OF THE INVENTION

1. Field of the Invention

The present invention relates generally to orthopedic prosthetic devices. More specifically, the invention relates to a femoral orthopedic knee implant for use in conjunction with a total knee arthroplasty ("TKA"), wherein the femoral component is designed to accommodate a broader range of knee flexion than femoral components known in the art.

2. Description of the Related Art

Disease and trauma affecting the articular surfaces of the knee joint are commonly effectively treated by surgically replacing the articulating ends of the femur and tibia with prosthetic femoral and tibial implants, referred to as total knee replacements ("TKR"). These implants are made of materials that exhibit a low coefficient of friction as they articulate against one another so as to restore normal, pain free, knee function.

As a knee joint moves through a ROM, the angle of the distal femur relative to the mechanical axis of the person's leg changes. During high flexion, this change is even more pronounced. For example, as a person's natural knee is moved through a ROM from about 0° to about 155°, the angle of femoral rotation about the transverse axis which is perpendicular to the mechanical axis of the person's leg may move from about 10° at to about 30°.

Most TKRs, however, include femoral components that are designed to accommodate knee joint articulation from a position of slight hyper extension to approximately 115° to 130° of flexion. However, the healthy human knee is capable of a range of motion ("ROM.") approaching 170° of flexion, and a ROM in around 155° is required for deep kneeling and squatting as may be required during some sporting, religious or cultural events.

There is a need, therefore, for an improved TKR femoral component that accommodates knee °flexion, under optimal conditions, of more than 130° ("high flexion").

SUMMARY OF THE INVENTION

The present invention comprises, in one embodiment thereof, an improved femoral prosthesis for a TKR. The femoral component of the TKR comprises an internal non-articulating bone contacting surface adapted to receive a resected distal femur. In a preferred embodiment, the bone contacting surfaces of the femoral component include anterior, distal, and posterior chamfer surfaces, which may further comprise bone growth promoting surfaces attached thereto.

The femoral component further comprises anterior, distal, medial posterior and, lateral posterior articulating portions, referred to herein as medial and lateral posterior condyles. The medial and lateral condyles each comprise a unique "height." The height of each condyle is measured from a line tangent to the distal articulating surface to the proximal tip of a particular condyle. The differences in the medial and lateral condylar height of a prosthetic femoral component according to the present invention permit a larger angle of femoral rotation in a TKR about the mechanical axis of a patient's leg. In addition, the extent to which the medial aspect of the lateral femoral condyle extends into the inter-condylar region of the femoral prosthetic component is reduced in the present invention to accommodate high flexion.

An advantage of the present invention is that it allows greater rotation of the distal femur about a leg's mechanical axis. This greater rotation is necessary to, and therefore accommodates, high flexion in a patient's knee.

Other advantages and features of the present invention will be apparent to those skilled in the art upon a review of the appended claims and drawings.

BRIEF DESCRIPTION OF THE DRAWINGS

The above-mentioned and other features and objects of this invention, and the manner of obtaining them, will become more apparent and the invention itself will be better understood by reference to the following description of an embodiment of the invention taken in conjunction with the accompanying drawings, wherein.

Figure 1:
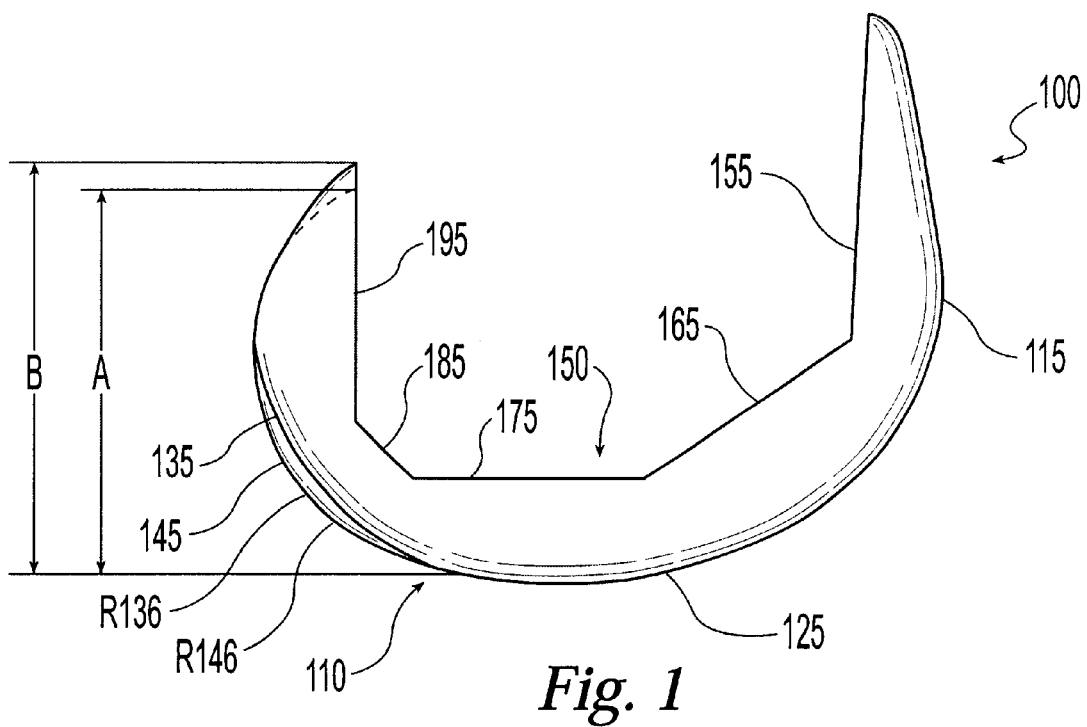
FIG. 1 is a side view of an embodiment of the present invention showing the difference in the medial and lateral condyle heights.

Corresponding reference characters indicate corresponding parts throughout the several views. Although the drawings represent an exemplary embodiment of the present invention, the drawings are not necessarily to scale and certain features may be exaggerated to better illustrate and explain the invention. The exemplification set out herein illustrates an exemplary embodiment of the invention only and such exemplification.

DETAILED DESCRIPTION OF THE INVENTION

As used herein, the following directional definitions apply. Anterior and posterior mean nearer the front or nearer the back of the body respectively. Thus, for the knee joint described herein, anterior refers to that portion of the knee that is nearer the front of the body, when the leg is in an extended position. Proximal and distal mean nearer to or further from the root of the structure, respectively. For example, the distal femur is a part of the knee joint while the proximal femur is closer to the hip joint. Finally, the adjectives medial and lateral mean nearer the sagittal plane or further from the sagittal plane respectfully. The sagittal plane is an imaginary vertical plane through the middle of the body that divides the body into right and left halves.

Referring initially to FIG. 1, a femoral component 100 of a TKR according to one embodiment of the present invention comprises an external articulating surface 110 and a bone contacting non-articulating internal surface 150. Articulating surface 110 comprises an anterior articulating surface 115, a distal articulating surface 125, a medial posterior condylar articulating surface 135, and a lateral articulating condylar surface 145.

Femoral component 100 may comprise any biocompatible material having the mechanical properties necessary to function as a human knee distal femoral prosthesis. Preferably, femoral component 100 comprises titanium, titanium alloy, cobalt chrome alloy, stainless steel, or a ceramic.

Figure 5:
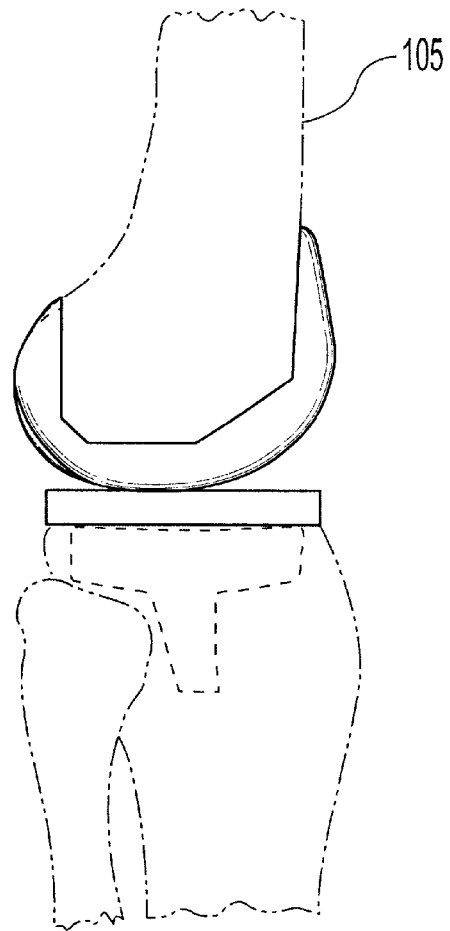
FIG. 5 is a superior view of the embodiment of FIG. 1, showing the rotation of the present invention between no flexion and high flexion.

The internal non-articulating portion of femoral component 100 is adapted to receive a resected distal femur 105, as shown in FIG. 5. The surgical cuts made to distal femur 105 can be made by any means, in any sequence and in any configuration known to those of skill in the art of knee arthroplasty. In a preferred embodiment, femoral component 100 comprises a plurality of chamfer surfaces corresponding to a plurality of chamfer surfaces made in distal femur 105. Surface 150 may comprise a porous metal surface or any surface likely to promote the growth of bone therein.

Non-articular surface 150 of femoral component 100 preferably comprises anterior non-articular surface 155, distal anterior non-articular surface 165, distal non-articular surface 175, two distal posterior non-articular surfaces 185, and two posterior non-articular surfaces 195.

Distal non-articular surface 175 is generally flat and adapted to receive the distal most surface of resected femur 105. Surface 175 comprises two opposing ends. One end of surface 175 abuts one end of distal anterior non-articular surface 165, which surface 165 also comprises two opposing ends. The remaining end of surface 165 extends from surface 175 anteriorly and superiorly such that an obtuse angle is formed between each surface 165 and surface 175. Anterior non-articular surface 155 extends superiorly from the remaining end of surface 165.

The opposing end of distal non-articular surface 175 abuts one end of each distal posterior non-articular surface 185, which surfaces 185 also comprise two opposing ends. The remaining end of surface 185 extends from surface 175 posteriorly and superiorly such that an obtuse angle is formed between each surface 165 and surface 175. Posterior non-articular surfaces 195 extend superiorly from the remaining ends of surfaces 185, respectively.

Referring still to FIG. 1, external articulating surface 110 of femoral component 100 comprises an anterior articulating surface 115, a distal articulating surface 125, a medial posterior condylar articulating surface 135, and a lateral posterior articulating condylar surface 145. The various articulating surfaces comprising articulating surface 110 of the present invention form a single curved surface having a vaiable radius adapted to engage cooperatively with a prosthetic knee meniscal component.

In the preferred embodiment of the present invention, condylar surfaces 135 and 145 comprise differing intermediate radii 136 and 146, respectively. The intermediate radius of each condylar surface is that portion of the articular surface between the distal articular surface and the posterior articular surface. The lateral condylar intermediate radius 36 is larger in the preferred embodiment than the medial intermediate radius 146.

Figure 2:
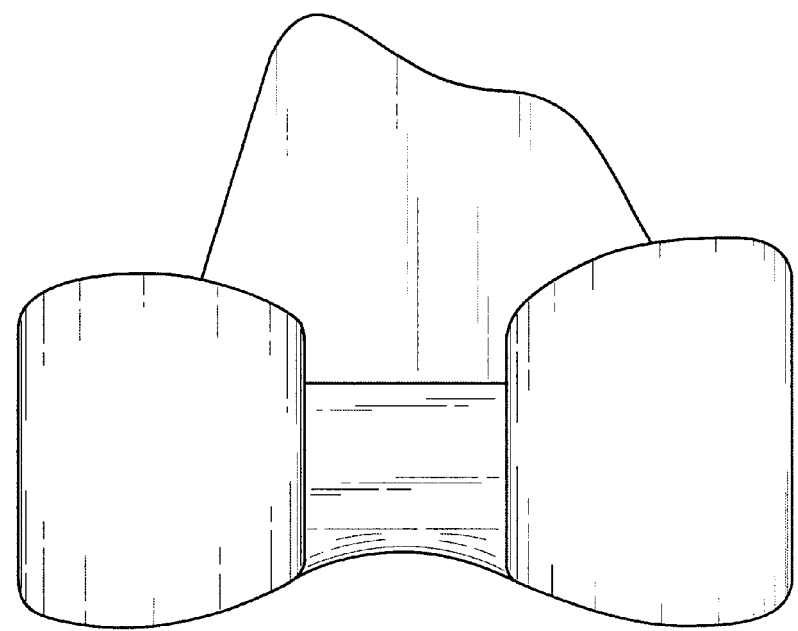
FIG. 2 is a posterior view of the embodiment shown in FIG. 1.

Referring again to FIG. 1, there is shown line 110 tangent to distal ticulating surface 125, and heights "A" and "B" showing the heights of medial and lateral condylar articulating surfaces 135 and 145, respectively. As shown in FIG. 1, the height A of lateral condyle 145 is less than the height, B, of medial condyle 135. This difference in condylar heights is also shown in FIG. 2. In the preferred embodiment, the difference in condylar heights is from about 1 mm to about 5 mm; however those of skill in the art will appreciate that a broad range of height differentials may be employed with the present invention.

Figure 3:
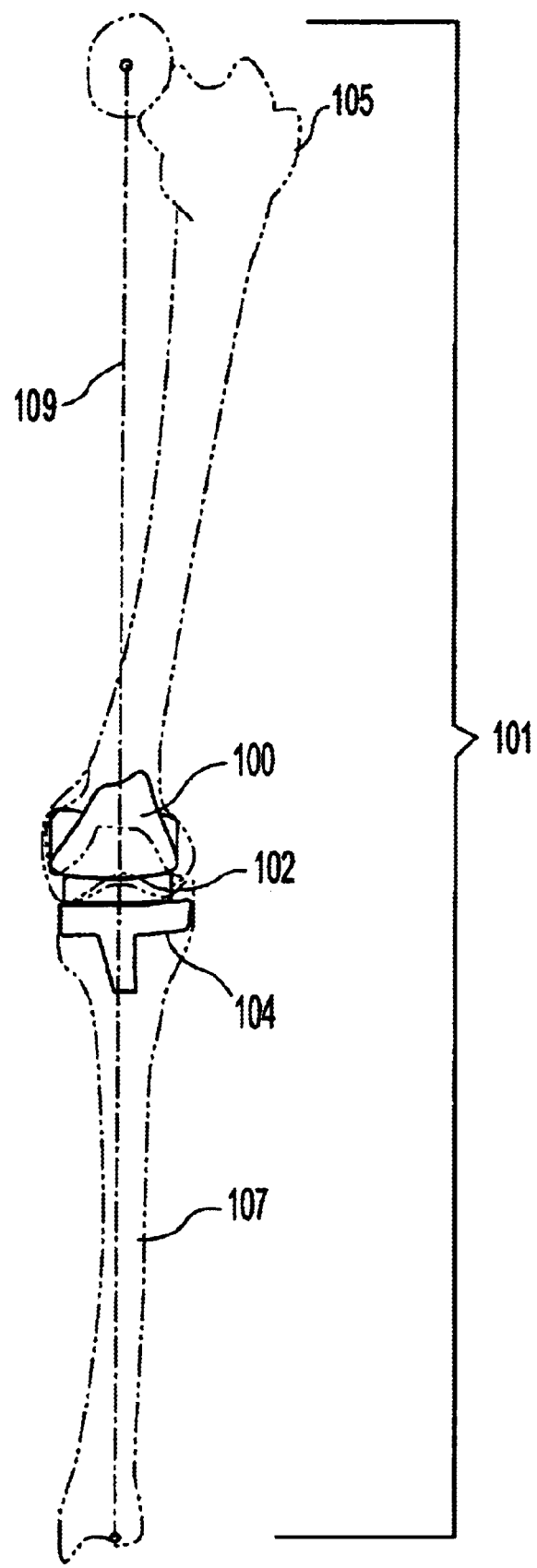
FIG. 3 is an anterior view of a human femur, tibia, knee joint, and leg mechanical axis.
Figure 4:
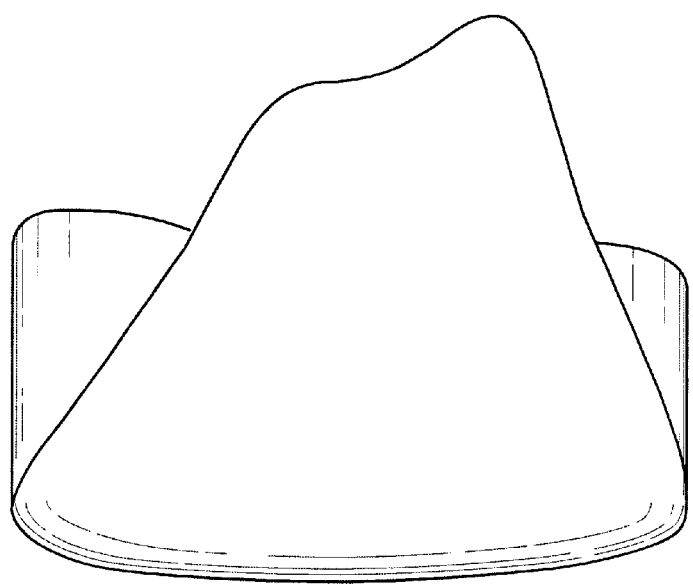
FIG. 4 is an anterior view of the embodiment shown in FIG. 1.

Referring now to FIG. 3, there is shown a front view of right leg 101 in full extension comprising femur 105, artificial femoral component 100, prosthetic meniscal component 102, prosthetic tibial component 104, and tibia 107. There is further shown line 109 representing the mechanical axis of leg 101. As leg 101 flexes, it is necessary for femoral component 100 to rotate medially about mechanical axis 109. The condylar height differential of femoral component 100 in the present invention allows sufficient rotation to accommodate high flexion. In addition, the width of lateral condyle 145 is truncated such that the distance between the lateral and medial sides of lateral condyle 135 is less than the distance between the lateral and medial sides of medial condyle 145 to further enhance the ability of femoral component 100 to achieve high flexion in a range from about 130° to 170°, or at least above about 150° without interfering with adjacent soft tissues.

It will be appreciated by those skilled in the art that the foregoing is a description of a preferred embodiment of the present invention and that variations in design and construction may be made to the preferred embodiment without departing from the scope of the invention as defined by the appended claims.

We claim:

1. A femoral component for a prosthetic knee, comprising: an internal non-articulating portion; and an external articulating portion, the articulating portion comprising a distal articulating surface, a medial posterior condyle and a lateral posterior condyle, wherein a length of the lateral posterior condyle measured from a line tangent to the distal articulating surface is less than a corresponding length of the medial posterior condyle.

2. The device of claim 1, wherein: the femoral component comprises a material selected from the group consisting of thermoplastic polymers, thermoset polymers, titanium, titanium alloy, tantalum, cobalt chrome alloy, stainless steel, and ceramics.

3. The device of claim 1, wherein the difference in medial and lateral condylar heights is within the range of about 1 mm to about 5 mm.

4. A femoral component for a prosthetic knee, comprising: an internal non-articulating portion; and an external articulating portion, wherein the articulating portion comprising a medial posterior condyle having a height and a lateral posterior condyle having a height, wherein the height of the lateral posterior condyle is less than the height of the medial posterior condyle; the femoral component further comprising an intermediate posterior medial condyle having a radius; and an intermediate posterior lateral condyle having a radius, wherein radius of the intermediate posterior of lateral condyle is less than the radius of the intermediate posterior medial condyle.

5. The device of claim 4, wherein: the femoral component comprises a material selected from the group consisting of titanium, titanium alloy, cobalt chrome alloy, stainless steel, and ceramics.

6. The device of claim 4, wherein the difference in medial and lateral condylar heights is within the range of about 1 mm to about 5 mm.

7. The device of claim 4, wherein the difference in medial and lateral intermediate radii is within the range of about 0.1 mm to about 20 mm.

8. A femoral component for a prosthetic knee, comprising: an internal non-articulating portion; and an external articulating portion, wherein the articulating portion comprising a medial posterior condyle having a height and a lateral posterior condyle having a height, wherein the height of the lateral posterior condyle is less than the height of the medial posterior condyle, an wherein the medial aspect of the lateral posterior condyle is truncated, such that the distance between the lateral and medial sides of the lateral condyle is less than the distance between the lateral and medial sides of the medial condyle; the femoral component further comprising an intermediate posterior medial condyle having a radius; and an intermediate posterior lateral condyle having a radius, wherein the radius of the intermediate posterior lateral condyle is less than the radius of the intermediate posterior medial condyle.

9. The device of claim 8, wherein: the femoral component comprises a material selected from the group consisting of titanium, titanium alloy, cobalt chrome alloy, stainless steel, and ceramics.

10. The device of claim 8, wherein the difference in medial and lateral condylar heights is within the range of about 1 mm to about 5 mm.

11. The device of claim 8, wherein the difference in medial and lateral intermediate radii is within the range of about 0.1 mm to about 20 mm.

* * * * *